United States Patent
Nobuto et al.

(10) Patent No.: US 8,636,812 B2
(45) Date of Patent: Jan. 28, 2014

(54) TWO-PART FOAM HAIR DYE

(75) Inventors: Yuko Nobuto, Kariya (JP); Yuki Naoi, Itabashi-ku (JP); Makoto Iijima, Mason, OH (US)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/812,914

(22) PCT Filed: Aug. 30, 2011

(86) PCT No.: PCT/JP2011/069606
§ 371 (c)(1),
(2), (4) Date: Jan. 29, 2013

(87) PCT Pub. No.: WO2012/029779
PCT Pub. Date: Mar. 8, 2012

(65) Prior Publication Data
US 2013/0125918 A1      May 23, 2013

(30) Foreign Application Priority Data
Aug. 31, 2010 (JP) .................. 2010-194571

(51) Int. Cl.
*A61Q 5/10* (2006.01)
(52) U.S. Cl.
USPC .............. 8/405; 8/406; 8/424; 8/435; 8/552; 8/594; 8/606
(58) Field of Classification Search
USPC .............. 8/405, 406, 424, 435, 552, 594, 606
See application file for complete search history.

(56) References Cited

U.S. PATENT DOCUMENTS

| | | |
|---|---|---|
| 3,341,418 A | 9/1967 | Moses et al. |
| 3,709,437 A | 1/1973 | Wright |
| 4,823,985 A | 4/1989 | Grollier et al. |
| 4,961,925 A | 10/1990 | Tsujino et al. |
| 5,143,518 A | 9/1992 | Madrange et al. |
| 5,651,793 A | 7/1997 | Hoeffkes et al. |
| 5,848,730 A | 12/1998 | Kawase et al. |
| 5,968,486 A | 10/1999 | Newell et al. |
| 6,692,539 B2 | 2/2004 | Desenne et al. |
| 7,083,655 B2 | 8/2006 | Pratt et al. |
| 7,938,864 B2 | 5/2011 | Miyabe et al. |
| 7,955,400 B2 | 6/2011 | Fujinuma et al. |
| 7,972,389 B2 | 7/2011 | Matsunaga et al. |
| 8,002,848 B2 | 8/2011 | Miyabe |
| 8,021,439 B2 | 9/2011 | Miyabe et al. |
| 8,025,702 B2 | 9/2011 | Fujinuma et al. |
| 8,025,703 B2 | 9/2011 | Ogawa et al. |
| 8,152,858 B2 | 4/2012 | Fujinuma et al. |
| 8,153,108 B2 | 4/2012 | Fujinuma et al. |
| 8,158,112 B2 | 4/2012 | Fujinuma et al. |
| 2002/0139957 A1 | 10/2002 | Matsuo et al. |
| 2003/0172473 A1 | 9/2003 | Desenne et al. |
| 2004/0213752 A1 | 10/2004 | Fujinuma et al. |
| 2004/0237218 A1 | 12/2004 | Marsh et al. |
| 2005/0125912 A1 | 6/2005 | Desenne et al. |
| 2007/0251029 A1 | 11/2007 | Bureiko et al. |
| 2008/0010754 A1 | 1/2008 | Bureiko et al. |
| 2010/0126522 A1 | 5/2010 | Fujinuma et al. |
| 2010/0126523 A1 | 5/2010 | Fujinuma et al. |
| 2010/0236570 A1 | 9/2010 | Fujinuma et al. |
| 2010/0242187 A1 | 9/2010 | Miyabe |
| 2010/0251488 A1 | 10/2010 | Fujinuma et al. |
| 2010/0257677 A1* | 10/2010 | Miyabe et al. ................ 8/405 |
| 2010/0299848 A1 | 12/2010 | Fujinuma et al. |
| 2010/0313905 A1 | 12/2010 | Fujinuma et al. |
| 2010/0316583 A1 | 12/2010 | Fujinuma et al. |
| 2011/0073128 A1 | 3/2011 | Ogawa et al. |
| 2011/0214682 A1 | 9/2011 | Fujinuma et al. |
| 2011/0277782 A1 | 11/2011 | Iijima et al. |
| 2012/0111974 A1 | 5/2012 | Fujinuma et al. |
| 2012/0186598 A1 | 7/2012 | Fujinuma et al. |
| 2012/0284932 A1 | 11/2012 | Naoi et al. |
| 2012/0305021 A1 | 12/2012 | Iijima et al. |

FOREIGN PATENT DOCUMENTS

| | | |
|---|---|---|
| CN | 1620279 A | 5/2005 |
| DE | 1801518 | 1/1971 |
| DE | 20 2004 021 806 | 3/2011 |

(Continued)

OTHER PUBLICATIONS

International Search Report Issued Dec. 6, 2011 in PCT/JP11/69606 Filed Aug. 30, 2011.
Submission of Publications and the like, dated Nov. 10, 2008, in Japanese Patent Application No. 2004-130373.
Corresponding application filed in Japanese Application No. 2004-130373, filed on Nov. 10, 2008.
Japanese Patent Office Communication. Apr. 21, 2009, 3 pp. (includes statement submitted by third party).
Submission of Publications and the like, dated Mar. 24, 2009, in Japanese Patent Application No. 2004-130373. (with English translation).
Submission of Publication and the like, dated Sep. 7, 2009, in Japanese Patent Application No. 2004-130373.
Shinbiyo Marcel. Oct. 1996. No. 31, pp. 73 and 83. "Vivid Highlight" advertisement page (with partial English translation).

(Continued)

*Primary Examiner* — Eisa Elhilo
(74) *Attorney, Agent, or Firm* — Oblon, Spivak, McClelland, Maier & Neustadt, L.L.P.

(57) ABSTRACT

A two-part foam hair dye which comprises a first part comprising an alkali agent, a second part comprising hydrogen peroxide, and a non-aerosol foamer container, wherein the first part comprises the components (A) to (D), an equivalent ratio of a anion site of the component (A) to a cation site of the component (B) (anion/cation) is more than 1, a mass ratio of a content of the component (C) to content of the component (D) ((C)/(D)) is 5 or less, and the liquid mixture has a viscosity (25° C.) of 1 to 300 mPa·s: (A) a carboxylic acid anion surfactant, (B) a polymer or copolymer having a mole fraction of diallyldimethyl quaternary ammonium salt monomer of 70% or more, (C) 0.5 to 1.5% by mass of an oxidation dye having a meta-dihydroxybenzene structure, and (D) 0.1 to 9% by mass of polypropyleneglycol of Mw 200 to 1200.

15 Claims, No Drawings

(56) References Cited

FOREIGN PATENT DOCUMENTS

| | | |
|---|---|---|
| EP | 113418 | 7/1984 |
| EP | 0 503 507 | 9/1992 |
| EP | 1 055 425 | 11/2000 |
| EP | 0 877 653 | 10/2002 |
| EP | 1291006 | 12/2003 |
| EP | 2 127 637 A1 | 12/2009 |
| EP | 2283803 A1 | 2/2011 |
| GB | 1125528 | 8/1968 |
| GB | 2 254 341 | 10/1992 |
| GB | 2 293 157 | 3/1996 |
| JP | 48-68750 | 9/1973 |
| JP | 49-050144 | 5/1974 |
| JP | 55-49308 | 4/1980 |
| JP | 58-30282 | 6/1983 |
| JP | 59-108710 | 6/1984 |
| JP | 61-143412 | 7/1986 |
| JP | 62-242609 | 1/1987 |
| JP | 62-242609 | 10/1987 |
| JP | 63-246313 | 10/1988 |
| JP | 04-99711 | 3/1992 |
| JP | 04-282307 | 10/1992 |
| JP | 04-282308 | 10/1992 |
| JP | 04-293568 | 10/1992 |
| JP | 06-107530 | 4/1994 |
| JP | 6-271435 | 9/1994 |
| JP | 06-271435 | 9/1994 |
| JP | 07-23293 | 3/1995 |
| JP | 07-267834 | 10/1995 |
| JP | 07-330559 | 12/1995 |
| JP | 07-330560 | 12/1995 |
| JP | 08-40837 | 2/1996 |
| JP | 8-119838 | 5/1996 |
| JP | 08-119839 | 5/1996 |
| JP | 08-165235 | 6/1996 |
| JP | 08-199188 | 8/1996 |
| JP | 8-199188 | 8/1996 |
| JP | 08-230959 | 9/1996 |
| JP | 08-231345 | 9/1996 |
| JP | 8-231346 | 9/1996 |
| JP | 08-259426 | 10/1996 |
| JP | 8-259426 | 10/1996 |
| JP | 08-268848 | 10/1996 |
| JP | 8-283695 | 10/1996 |
| JP | 09-2923 | 1/1997 |
| JP | 09-2925 | 1/1997 |
| JP | 9-25223 | 1/1997 |
| JP | 09-40534 | 2/1997 |
| JP | 2579516 | 2/1997 |
| JP | 9-100222 | 4/1997 |
| JP | 09-136818 | 5/1997 |
| JP | 09-143040 | 6/1997 |
| JP | 09-506130 | 6/1997 |
| JP | 09-227347 | 9/1997 |
| JP | 9-227347 | 9/1997 |
| JP | 09-234112 | 9/1997 |
| JP | 9-255541 | 9/1997 |
| JP | 09-255541 | 9/1997 |
| JP | 09-301835 | 11/1997 |
| JP | 9-301835 | 11/1997 |
| JP | 10-25230 | 1/1998 |
| JP | 10-167938 | 6/1998 |
| JP | 10-287534 | 10/1998 |
| JP | 10-324357 | 12/1998 |
| JP | 11-18836 | 1/1999 |
| JP | 11-18837 | 1/1999 |
| JP | 11-50089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-246369 | 9/1999 |
| JP | 11-286421 | 10/1999 |
| JP | 11-349453 | 12/1999 |
| JP | 2000-191471 | 7/2000 |
| JP | 2000-128215 | 9/2000 |
| JP | 2000-297018 | 10/2000 |
| JP | 2000-297019 | 10/2000 |
| JP | 2001-10930 | 1/2001 |
| JP | 2001-19626 | 1/2001 |
| JP | 2001-39460 | 2/2001 |
| JP | 2001-97834 | 4/2001 |
| JP | 2001 131034 | 5/2001 |
| JP | 2001-172166 | 6/2001 |
| JP | 2001-278742 | 10/2001 |
| JP | 2001-288054 | 10/2001 |
| JP | 2001-327321 | 11/2001 |
| JP | 2002-20247 | 1/2002 |
| JP | 2002-97121 | 4/2002 |
| JP | 2002-154938 | 5/2002 |
| JP | 2002-193771 | 7/2002 |
| JP | 2002-201118 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 03-12479 | 1/2003 |
| JP | 2003-26554 | 1/2003 |
| JP | 2003-40747 | 2/2003 |
| JP | 2003-63936 | 3/2003 |
| JP | 2003-73240 | 3/2003 |
| JP | 2003-73241 | 3/2003 |
| JP | 2003-081791 A | 3/2003 |
| JP | 2003-95900 | 4/2003 |
| JP | 2003 192551 | 7/2003 |
| JP | 2003 342139 | 12/2003 |
| JP | 2004 339216 | 12/2004 |
| JP | A1-2007-291015 | 11/2007 |
| JP | A1-2007-314523 | 12/2007 |
| JP | 2008 537963 | 10/2008 |
| JP | 2008 266344 | 11/2008 |
| JP | 2009 541300 | 11/2009 |
| JP | 2010-6803 | 1/2010 |
| JP | 2010 6805 | 1/2010 |
| JP | 2010-6805 | 1/2010 |
| JP | 2011 132228 | 7/2011 |
| WO | WO 91/14759 | 10/1991 |
| WO | WO 95/16023 | 6/1995 |
| WO | WO 01/85105 | 11/2001 |
| WO | WO 01/85113 | 11/2001 |
| WO | WO 2009/144952 A1 | 12/2009 |
| WO | 2010 103795 | 9/2010 |
| WO | 2010 103796 | 9/2010 |
| WO | 2011 065550 | 6/2011 |

OTHER PUBLICATIONS

Vivid Highlight. Iriya Cosmetics. Packaging and Instructions Insert. Sep. 6, 1996 (with English translation).
Hair Mode. Aug. 1996. No. 437, p. 108. (with partial English translation).
Decision to Refuse a European Patent Application issued Apr. 19, 2011, in regard to European Patent Application No. 08752171.2, filed Apr. 25, 2008.
Third-Party Observation submitted Jun. 3, 2011, in European Patent Application No. 10172766.7, filed Apr. 26, 2004.
Rompps Chemie Lexikon, vol. 6, $8^{th}$ Ed. 1998. p. 4531.
Third-Party Observation submitted May 3, 2011, in European Patent Application No. 0 400 9836.0.
Extended European Search Report issued Apr. 7, 2011, in European Application No. 10183376.2.
European Patent Office Communication pursuant to Rule 114(2) EPC issued May 3, 2011, in European Application No. 04009836.0 filed Apr. 26, 2004.
Third-Party Observation filed on Apr. 27, 2011, in European Patent Application No. 0 400 9836.0 (including translation of submission).
Food and Packaging. vol. 34, No. 8. "Can Technology Study Group." Aug. 1, 1993. 6 pages.
Notification of Reason for Refusal, dated Jul. 22, 2008, in Japanese Patent Application No. 2004-130373.
English translation of Submission of Publication and the like, dated Dec. 25, 2007, in Japanese Patent Application No. 2004-130373.

(56) References Cited

OTHER PUBLICATIONS

English translation of Submission of Publication and the like, dated Feb. 29, 2008, in Japanese Patent Application No. 2004-130373.
Extended European Search Report issued in Nov. 4, 2010 in European Patent Application No. 10172766.7.
Taya-A.T. HM Education Mook., Series 3. "Knowing Mechanisms of Hair Coloring Agents." Apr. 10, 1998. pp. 8-9. (with English translation).
Nakanishi, Fumio. Fragrance Journal. "Future View of Hair Care Products." Jan. 15, 1997. pp. 49-56. (with English translation).
Sato, Takatoshi, et al. Fragrance and Cosmetics Science. "Permanent Hair Colorant." Sep. 20, 2001. pp. 138-140. (with English translation).
Watanabe, Yasushi, et al. Hair Science. "Hair Colorant." Feb. 1, 1986. pp. 144-150. (with English translation).
Submission of Publications and the like, filed Oct. 18, 2010 in Japanese application No. 2004-130373 (w/ English Translation).
Communication Pursuant to Article 94(3) EPC issued Nov. 5, 2010 in European Patent application No. 0 400 9836.0.
Submission of Publications and the like, filed Oct. 25, 2010 in Japanese application No. 2008-270377 (w/ English Translation).
Decision of Refusal issued Jun. 16, 2010 in Japanese application No. 2004-130373 (w/ English Translation).
Written Demand for Appeal filed Sep. 10, 2010 in Japanese application No. 2004-130373 (w/ English Translation).
Amendment filed Sep. 10, 2010 in Japanese application No. 2004-130373 (w/ English Translation).
Submission of Publications and the like, filed Apr. 8, 2009 in Japanese application No. 2004-130373 (w/ English Translation).
English Translation of Decision to Grant a Patent issued Jan. 4, 2011 in Japanese Patent application No. 2004-130373 w/ Copy of Allowed Claims.
English Translation of Decision to Grant a Patent issued Jan. 4, 2011 in Japanese Patent application No. 2008-270377 w/ Copy of Allowed Claims.
English translation of Remarks filed Oct. 20, 2008 in Japanese application No. 2004-130373.
English translation of Remarks filed Mar. 9, 2009 in Japanese application No. 2004-130373.
English translation of Amendment filed Mar. 9, 2009 in Japanese application No. 2004-130373.
European Search Report submitted Aug. 23, 2004, in European Patent Application No. 04009836.0.
English translation of Submission of Publications filed Nov. 10, 2008 in Japanese application No. 2004-130373.
English translation of Notification of Reasons for Refusal issued Jan. 6, 2009 in Japanese application No. 2004-130373.
English translation of Submission of Publications filed Dec. 25, 2007 in Japanese application No. 2004-130373.
English translation of Submission of Publications filed Feb. 29, 2008 in Japanese application No. 2004-130373.
Response to Communication Pursuant to Article 96(2) EPC filed Apr. 25, 2007 in European Patent application No. 0 400 9836.0.
Communication Pursuant to Article 94(3) EPC issued Dec. 29, 2008 in European Patent application No. 0 400 9836.0.
Response to Communication filed Jul. 8, 2009 in European Patent application No. 0 400 9836.0.
Third-Party Observation filed on Dec. 19, 2009 in European Patent application No. 0 400 9836.0.
Observations under Rule 114(2) EPC filed Apr. 9, 2010 in European Patent application No. 0 400 9836.0.
Third-Party Observation filed on May 10, 2010 in European Patent application No. 0 400 9836.0.
Communication Pursuant to Article 94(3) EPC issued Jun. 28, 2010 in European Patent application No. 0 400 9836.0.
Response to Communication filed Aug. 10, 2010 in European Patent application No. 0 400 9836.0.
Amendment filed Dec. 5, 2008 in European Patent application No. 0 400 9836.0.
Response to Communication filed Feb. 18, 2011 in European Patent application No. 0 400 9836.0.
Remarks filed Feb. 25, 2011 in European Patent application No. 08 752 171.2.
Experimental Report 1 (with English translation), served on May 24, 2011, in regard to Heisei 23 year (Yo) No. 22009.
Nakanishi, Fumio. Fragrance Journal. "Function of Recent Hair Coloring Agent and Developmental Trend Thereof." Aug. 15, 2001. pp. 39-45. (with English translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).
Tashima, Masaru, et al. Fragrance Journal. "Research and Development of Mist Foam Type Hair Styling Product." Dec. 15, 1992. pp. 61-69. (with English translation).
Omura, Takayuki, et al. Fragrance Journal. "Development Trend and Problems of Recent Hair Foam." Mar. 15, 1994. pp. 29-35. (with English translation).
Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 36, No. 3. Non-Gas Container Having Increased Level of Accomplishment (Part 3). 1995. pp. 154-158. (with English translation).
Prettia Product Information (with English Translation), Kao Corporation, published after Apr. 23, 2003. (served on May 25, 2011 in regard to Heisei 23 year (Yo) No. 22009).
Instructions for Feminine Treatment Hair Color (with English Translation), Feminine Co., Ltd., published before Apr. 23, 2003 (served on May 25, 2011 in regard to Heisei 23 year (Yo) No. 22009).
Feminine Treatment Hair Color 84, Certification for Approval for Manufacture of Quasi-Drug (with English Translation), Jan. 30, 1997.
Instructions for Feminine Retouch Color (with English Translation), Feminine Co., Ltd., published before Apr. 23, 2003. (served on May 25, 2011, in regard to Heisei 23 year (Yo) No. 22009).
Experimental Report 2 (with English translation), served on May 25, 2011, in regard to Heisei 23 year (Yo) No. 22009.
Experimental Report 3 (with English translation), served on May 25, 2011, in regard to Heisei 23 year (Yo) No. 22009.
Test Report 4 (with English translation), served on Jul. 10, 2011, in regard to Heisei 23 year (Yo) No. 22009.
Mottram, F.J., et al. Poucher's Perfumes, Cosmetics and Soaps, $10^{th}$ ed. © 2000. "Hair Shampoos." pp. 295-301.
Handbook "Poly Haarberater Coloration," original edition, 1992. pp.76-77.
Third-Party Observation submitted May 12, 2011, in European Patent Application No. 04009836.0.
371-EPO Response in European Patent Application No. 04009836.0, Jul. 15, 2011.
Reply to EESR in European Patent Application No. 10172766.7, Apr. 29, 2011.
Third-Party Observation submitted Jun. 24, 2011, in European Patent Application No. 10172766.7.
Third-Party Observation submitted Jun. 24, 2011, in European Patent Application No. 10183376.2.
Photocopy of a folding, collapsible box for "Poly Brillance Intensiv-Color-Creme", dated as Aug. 25, 1997.
Instructions for use contained in the folding, collapsible box for "Poly Brillance Intensiv-Color-Crème" Aug. 25, 1997.
Entire contents of the folding, collapsible box for "Poly Brillance Intensiv-Color-Crème" Aug. 25, 1997.
Close-up photocopy of the folding, collapsible box for "Poly Brillance Intensiv-Color-Crème" Aug. 25, 1997.
Miyagi, Takashi. Food and Packaging, vol. 42, No. 10. "Growing Pump Foamer Spreading into Western Markets, Part One: Mini-Foamer." Oct. 1, 2001. pp. 609-613. (with English translation).
Kishi, Haruo. Modern Fragrance and Cosmetics Science, $1^{st}$ Edition. Mar. 20, 1979. pp. 42-47. (with English translation).

(56) References Cited

OTHER PUBLICATIONS

Cosmetics Handbook. Nov. 1, 1996. pp. 220-221, 441-444. (with English translation).
Handbook—Raw Materials of Cosmetics and Drugs—revised edition. Feb. 1, 1977. pp. 358-361. (with English translation).
Yasuda, Kosaku, et al. Knowledge of Fat and Oil Products. Aug. 25, 1977. pp. 240-244. (with English translation).
Mitsui, Takeo. New Cosmetic Science. Jan. 12, 1993. pp. 137-142. (with English translation).
The Handbook of Oil Chemistry, $4^{th}$ ed. "Lipids and Surfactants." Nov. 20, 2001. p. 522. (with English translation).
Comprehensive Dictionary of Chemistry. Oct. 20, 1989. pp. 56, 60-61, 646-647, 1762-1763. (with English translation).
Sato, Takatoshi, et al. Fragrance and Cosmetics Science. Mar. 20, 1997. pp. 73-74. (with English translation).
Japanese Collection of General Raw Materials for Cosmetics, fourth edition. Oct. 31, 1997. p. 583. (with English translation).
Analytical Chemistry Handbook, revised second edition. Oct. 10, 1971. pp. 27-29. (with English translation).
Analysis Methods for Surfactants. Oct. 1, 1975. pp. 117-118. (with English translation).
Chemical Daily. "Surfactant—Penetrated to the various fields taking advantage of unique characteristics." Jan. 21, 1999. (with English translation).
The Nikkan Kogyo Shimbun, Ltd. "Nonylphenol Identified as Endocrine Disrupting Chemical." Aug. 6, 2001. (with English translation).
Chemical Daily. "Surfactant—Started growing responding to safety requirement." Jan. 19, 2000. (with English translation).
Chemical Daily. "Surfactant—Remarkable performance of nonionic surfactant (Market conditions in chemicals)." Jan. 25, 2002. (with English translation).
Nakanishi, Fumio, et al. Science History of Hair Dye. Jan. 8, 1991. pp. 45-47. (with English translation).
Experiment Result Report 1 (with English translation), prepared on Jul. 11, 2011, in regard to No. 22009, 2011 (yo).
Experiment Result Report 2 (with English translation), prepared on Jul. 22, 2011, in regard to No. 22009, 2011 (yo).
Declaration by Akiko Nagabuchi (with English translation), served on Sep. 21, 2011, in regard to No. 22009, 2011 (yo).
Experiment Result Report 5 (with English translation), served on Sep. 21, 2011, in regard to No. 22009, 2011 (yo).
Arai, Yasuhiro. "State-of-the-art: Hair Color Technology—Trends in development as seen in patents." Published by Fragrance Journal Ltd. Aug. 25, 2004. pp. 102-105, 212-213. (with English translation).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).
Written Argument filed by the Debtor (1/2) in The Case of Request for Provisional Disposition of Patent Right: No. 22056, 2011 (yo), served on Sep. 6, 2011. pp. 1-5, 29-34. (with partial English translation).
Amendments to the Claims in Japanese Patent Application No. 2010-268209, filed on Apr. 8, 2011. (with English translation).
Publication of Unexamined Patent Application JP 2003-81369, Mar. 19, 2003.
English translation of Submission of Publications and the like, filed Mar. 24, 2009, in Japanese Application No. 2004-130373.
English translation of Submission of Publications and the like, filed Nov. 10, 2008, in Japanese Application No. 2004-130373.
English translation of Notification of Reasons for Refusal issued Jul. 22, 2008, in Japanese Application No. 2004-130373.
English translation of Submission of Publications and the like, filed Sep. 7, 2009, in Japanese Application No. 2004-130373.
English translation of Submission of Publications and the like, filed Feb. 29, 2008, in Japanese Application No. 2004-130373.
English translation of Submission of Publications and the like, filed Dec. 25, 2007, in Japanese Application No. 2004-130373.
Comprehensible Surfactant, first edition. Sep. 1, 2003. pp. 32-49. (with English translation).
Quasi Drugs Manufacturing Material Specification 2006, first edition. pp. 527-528. Jun. 16, 2006. (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
Sato, Takatoshi. Science of Cosmetics. Mar. 20, 1997. pp. 138-140. (with English translation).
Denavarre, Maison G. The Chemistry and Manufacture of Cosmetics, second edition, vol. 4. 1975. pp. 841-863.
Cosmetics Dictionary, first edition. Oct. 1, 1992. p. 373. (with English translation).
New Cosmetic Science, second edition. Jan. 18, 2001. pp. 152-153. (with English translation).
"Make Your Hair Beautiful by Correct Usage—Hair Coloring ABC, revised edition." Feb. 1, 2000. pp. 18-19. (with English translation).
Robbins, Clarence R. "Chemical and Physical Behavior of Human Hair, fourth edition." Jul. 10, 2006. pp. 221-231. (with English translation).
Experimental Result Report 8 (with English translation), served on Nov. 29, 2011, in regard to No. 22009, 2011 (yo).
Fragrance Journal. vol. 19, No. 6. "Recent Progress of Hair Dyes and Problems in Research and Development." Jun. 15, 1991. pp. 26-27. (with English translation).
Miyagi, Takashi. Food and Packaging, vol. 34, No. 9. Will Non-Gas Containers Create a Boom? (No. 3) 1993. pp. 531-535. (with English translation).
Extended Search Report issued Nov. 4, 2010, in European Application No. 10172766.7.
Submission of Publication issued Oct. 18, 2010, in JP Application No. 2004-130373 (with English translation).
Office Action issued Nov. 5, 2010, in EP Application No. 04 009 836.0.
Third Party Observation issued on May 3, 2011, in corresponding European Application No. 04 009 836.
Iwakura, Ryouhei. "Present State and Problems of Hair Dyes." Fragrance Journal, Special Issue. No. 11, pp. 87-93. Dec. 25, 1990. (with English translation).
Ishikawa, Ryoji. Experimental Report, in regard to No. 22056, 2011 (yo). Dec. 28, 2011 (with English translation).
Declaration by Hattori, Nobuhito, in regard to No. 22056, 2011 (yo), served on Dec. 28, 2011 (with English translation).
Unichemy Corp. Experimental Report, in regard to No. 22056, 2011 (yo). Issued on Jun. 24, 2011 (with English translation).
Pharmaceutical Additive Dictionary, $2^{nd}$ edition. pp. 153-154, 203-205. Mar. 25, 2002. (with English translation).
Murata, Seishiro. Cosmetic Dictionary, $1^{st}$ edition. pp. 182-183, 666-667. Dec. 15, 2003. (with English translation).
Miyagi, Takashi. Food and Container, vol. 35, No. 10. pp. 588-593. 1994. (with English translation).
Miyagi, Takashi. Food and Container, vol. 35, No. 11. pp. 624-627. 1994. (with English translation).
Henkel Study Report, Study No. 1100546-2. "Single Application Epicutaneous Patch Test ($2^{th}$ Patch Test)," served on Jan. 30, 2012, in regard to No. 22009, 2011 (yo).
Henkel Study Report, Study No. 1100546-1. "Open Epicutaneous Test," served on Jan. 30, 2012, in regard to No. 22009, 2011 (yo).
Henkel Study Report. "In Vitro Skin Irritation Test: Human Skin Model Test," served on Jan. 30, 2012, in regard to No. 22009, 2011 (yo).
Study Report, No. 1100547-1, "Dermatological Use Test with Hair-Coloring Products in Split Design," served on Jan. 30, 2012, in regard to No. 22009, 2011 (yo).
Experimental Result Report 13 (with English translation), served on Jan. 30, 2012, in regard to No. 22009, 2011 (yo).
Excerpt from the Internet Website: www.bagonvalve.com in regard to Request Cancelation in Utility Model 20 2004 021 775, served on Apr. 18, 2012, (3 pp.).

(56) References Cited

OTHER PUBLICATIONS

Dr. Matthias Schweinsberg, Test Report: Foaming Characteristics and Flow Characteristics of Cosmetic Products According to EP 1 291 006 A1, Feb. 17, 2012 with English Translation, served on Apr. 17, 2012 in regard to DE litigation No. 4a O28/11.

Test Report dated May 1, 2012, Hoyu Co., Ltd., Product Development Laboratory of General Research & Development Institute, Section Chief: Ryouji Ishikawa, served on May 11, 2012 in regard to No. 5260, 2012 (wa) with English translation, (13 pp.).

European Patent Office Communication issued Mar. 12, 2012 in European Patent Application 04 009 836.0.

New Cosmetics Studies, dated Jan. 18, 2001, pp. 470-475 (with English Translation).

Packaging and Instructions Insert of VENEZEL Single-Solution Straight Perm (Dariya Corporation), with English Translation, 6 pp.

\* cited by examiner

TWO-PART FOAM HAIR DYE

FIELD OF THE INVENTION

The present invention relates to a two-part foam hair dye.

BACKGROUND OF THE INVENTION

Conventionally, a hair bleach product and a hair dye product are widely available in the form of liquid or cream. However, it is difficult for those who are not accustomed to using such a product to evenly apply it to the hair. This is because the viscosity of a mixture to be applied to the hair is adjusted relatively high, namely, to approximately 1000 to 10000 mPa·s, for prevention of dripping while the mixture is left on the hair. This makes it difficult to evenly spread the mixture and to adequately cover the hair root with the mixture. Furthermore, skills such as blocking and two-mirror technique are necessary for application of the mixture to the hair root and the back of the head, also requiring much time.

In contrast, a non-aerosol type foamer container discharging a liquid mixture of a two-part type hair bleach product or a two-part type hair dye product contained therein in the form of a foam is proposed (Patent Document 1). The above hair bleach product or hair dye product discharges a liquid mixture of the first part and the second part from a non-aerosol type foamer container in the form of a foam, whereby the liquid mixture is evenly applied to the hair, resulting in an evenly-colored finish. The above hair bleach product or hair dye product is particularly useful for resolving color differences between a newly-grown part and an already-dyed part. For these reasons, it is supported by a wide range of customers, regardless of sex and age groups.

However, the two-part type hair bleach product and the two-pack type hair dye product in the form of a foam of Patent Document 1 have various problems peculiar to a non-aerosol type foamer container discharging its content in the form of a foam such as lowered foaming properties (foam quality) under specific conditions. Also, because such a hair dye product has extremely lower viscosity in the state of a liquid mixture as compared to a conventional liquid or cream (hereinbelow, referred to as "conventional type") hair dye product, there has also been a limitation of formulation that a composition having good storage stability has to be designed. Furthermore, the two-part type hair bleach product and the two-part type hair dye product in the form of a foam of Patent Document 1 tend to have less sufficient fastness to shampooing than that of a conventional type. This would be because the hair dye product is applied to the hair in the form of a foam, the amount of the hair dye directly contributing to dyeing is smaller than the amount of the hair dye actually applied, and because the area of the air-liquid surface of the above product is larger than that of a conventional type, ammonia serving as an alkali agent readily volatilizes, leading to an insufficient amount of the alkali agent for full penetration of the dye into the center of the hair.

In contrast, as a conventional type two-part type hair dye product, a two-part type hair dye product containing polyoxyalkylene ether carboxylic acid or a salt thereof and a cationic polymer or an amphoteric polymer having no less than a certain level of cationic charge density is proposed (refer to Patent Document 2). According to this document, the two-part type hair dye product disclosed therein can impart a favorable hue. However, there is no description pertaining to a two-part type hair dye product provided by a non-aerosol type foamer container discharging a liquid mixture contained therein in the form of a foam. Further, this document is also undescribed and unsuggestive of a problem or limitation peculiar to a two-part type hair dye product prepared in the aforementioned form such as foaming properties (foam quality), storage stability and fastness to shampooing.

Also, a less irritating shampoo composition containing alkyl ether acetate and a cationic polymer exhibiting excellent hair color fading-preventing effects, foaming, smoothness when running fingers through the hair while shampooing, and smoothness during rinsing is proposed (Patent Document 3). However, this document neither teaches nor suggests the ratio of the cationic monomer in the cationic polymer. Further, because this document relates to an invention of a shampoo composition, there is no description or suggestion regarding application to a hair dye product. Basically, this invention relates to a technique to prevent color fading of the hair dyed with a hair color by use of this shampoo composition, and irrespective of the shampoo used, the technical concept per se is entirely different from provision of a hair dye product excellent in fastness to shampooing.

CITATION LIST

Patent Documents

[Patent Document 1] JP-A-2004-339216
[Patent Document 2] JP-A-2003-192551
[Patent Document 3] JP-A-2001-131034

SUMMARY OF THE INVENTION

The present invention provides a two-part foam hair dye which comprises a first part comprising an alkali agent, a second part comprising hydrogen peroxide, and a non-aerosol foamer container for discharging a liquid mixture of the first part and the second part in the form of a foam, wherein the first part comprises components (A) to (D), the equivalent ratio of the anion site of the component (A) to the cation site of the component (B) (anion/cation) is more than 1, a mass ratio of the content of the component (C) to the content of the component (D) ((C)/(D)) is 5 or less, and a viscosity of the liquid mixture at 25° C. is 1 to 300 mPa·s:

(A) a carboxylic acid anionic surfactant,
(B) a polymer or copolymer having a mole fraction of diallyldimethyl quaternary ammonium salt monomer of not less than 70%,
(C) 0.5 to 1.5% by mass of an oxidation dye having a meta-dihydroxybenzene structure, and
(D) 0.1 to 9% by mass of polypropyleneglycol of a weight-average molecular weight of 200 to 1200.

DETAILED DESCRIPTION OF THE INVENTION

The present inventors studied a variety of components of a non-aerosol type two-part foam hair dye in order to increase fastness to shampooing. As a result, they have found that it is beneficial to employ a carboxylic acid anionic surfactant and a polymer or copolymer containing a certain mole fraction or more of diallyldimethyl quaternary ammonium salt monomer in combination. Meanwhile, in order to produce a darkish color, an oxidation dye having a meta-dihydroxybenzene structure is often contained at a high concentration irrespective of the type of a hair dye.

In this study, the present inventors have newly found that when a carboxylic acid anionic surfactant, a polymer or copolymer having a mole fraction of diallyldimethyl quaternary ammonium salt monomer of not less than 70%, and a high concentration of an oxidation dye having a meta-dihydroxybenzene structure coexist in the first part of a non-aerosol type two-part foam hair dye, storage stability at low temperature was decreased.

The present invention relates to a two-part foam hair dye having good storage stability at low temperature and good foaming properties of a liquid mixture, while retaining the merit of a non-aerosol two-part foam hair dye, which is to be evenly applied to the hair to give an evenly-colored finish. Furthermore, the two-part foam hair dye has good dyeability, and after dyeing, it exhibits excellent fastness to shampooing, irrespective of the kind of shampoo used for shampooing.

The present inventors have found that even with the composition described above, storage stability at low temperature is remarkably improved, while high fastness to shampooing is maintained by using polypropyleneglycol having a certain range of weight-average molecular weight with the aforementioned oxidation dye at a certain range of mass ratio. Moreover, they have found that regardless of the formulation comprising a carboxylic acid anionic surfactant, which is relatively slightly inferior in foaming ability, and additionally comprising a high concentration of dye, which affects the foam sustainability, the two-part foam hair dye provides not only improved foam quality, but also good hair dyeability.

[Alkali Agent]

As the alkali agent comprised in the first part, for example, ammonia, alkanolamine such as monoethanolamine, sodium hydroxide, and potassium hydroxide can be used. Also, an ammonium salt such as, for example, ammonium bicarbonate, ammonium carbonate, and ammonium chloride and carbonate such as potassium carbonate and sodium bicarbonate can be added as a buffer as appropriate.

The pH of the liquid mixture of the first part and the second part in the two-part foam hair dye of the present invention is preferably 8 to 11, more preferably 8.5 to 10.5, and the amount of the alkali agent used is appropriately adjusted so that the liquid mixture achieves the aforementioned pH.

[Hydrogen Peroxide]

The content of hydrogen peroxide in the second part is preferably 1 to 9% by mass, more preferably 3 to 6% by mass, and the content of hydrogen peroxide in a liquid mixture of the first part and the second part is preferably 1 to 6% by mass, more preferably 2 to 5% by mass. Also, the pH of the second part is preferably 2 to 6, more preferably 2.5 to 4 in order to prevent decomposition of hydrogen peroxide during storage.

[(A): Carboxylic Acid Anionic Surfactant]

The two-part foam hair dye of the present invention at least comprises (A) a carboxylic acid anionic surfactant in the first part. Examples of the carboxylic acid anionic surfactant of the component (A) include an N-acylamino acid salt, an N-acyl-N-alkylamino acid salt, an amide type N-acylamino acid salt, an ether carboxylic acid salt, a sulfosuccinic acid ester salt, a fatty acid salt, alkyl succinate, and alkenyl succinate. Among them, an N-acylamino acid salt, an N-acyl-N-alkylamino acid salt, an ether carboxylic acid salt, and a sulfosuccinic acid ester salt are preferable.

Examples of an amino acid residue of the N-acylamino acid salt of the present invention include glutamic acid and aspartic acid, and examples of an amino acid residue of the N-acyl-N-alkylamino acid salt include glutamic acid, glycine, and β-alanine. Also, examples of an alkyl group of the N-acyl-N-alkylamino acid salt include a methyl group, an ethyl group, a propyl group, and an isopropyl group. Also, examples of an acyl group of the N-acylamino acid salt and N-acyl-N-alkylamino acid salt include a lauroyl group, a myristoyl group, and a palmitoyl group, and examples of the N-acylamino acid salt and the N-acyl-N-alkylamino acid salt include a sodium salt, a potassium salt, a lithium salt, an ethanolamine salt, a diethanolamine salt, and a triethanolamine salt (hereinafter referred to as TEA). Preferred specific examples of the N-acylamino acid salt include N-lauroyl glutamate, N-myristoyl glutamate, N-stearoyl glutamate, N-cocoyl glutamate, and N-hydrogenated tallow glutamate, and preferred specific examples of the N-acyl-N-alkylamino acid salt include an N-lauroyl-N-isopropyl glycine salt, an N-lauroyl sarcosine salt, an N-myristoyl sarcosine salt, an N-palmitoyl sarcosine salt, and an N-lauroyl-N-methyl-β-alanine salt.

Examples of the ether carboxylic acid salt include a polyglyceryl alkyl ether acetic acid salt or an ether acetic acid salt represented by the following general formula (1):

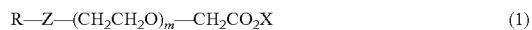

$$R-Z-(CH_2CH_2O)_m-CH_2CO_2X \quad (1)$$

wherein, R represents a linear or branched alkyl group or alkenyl group having a carbon number of 7 to 19, Z represents —O— or —CONH—, X represents a hydrogen atom, an alkali metal, triethanolamine, or ammonium, and m represents a number of 1 to 20.

In the aforementioned ether acetic acid salt, the carbon number of R is preferably 11 to 15. Also, m is preferably 3 to 15, more preferably 6 to 12. Specific examples thereof include polyoxyethylene (10) lauryl ether acetic acid (in the general formula (1), R=$C_{12}H_{25}$, Z=—O—, m=10), polyoxyethylene (8) myristyl ether acetic acid (in the general formula (1), R=$C_{14}H_{29}$, Z=—O—, m=8), lauric acid amide polyoxyethylene (6) ether acetic acid (in the general formula (1), R=$C_{11}H_{23}$, Z=—CONH—, m=6), lauric acid amide polyoxyethylene (10) ether acetic acid (in the general formula (1), R=$C_{11}H_{23}$, Z=—CONH—, m=10). Also, the degree of neutralization of the ether acetic acid salt is preferably 60 to 120%, and the counter ion X is preferably an alkali metal, especially potassium. Examples of the ether acetic acid salt include a polyoxyethylene tridecyl ether acetic acid salt and a polyoxyethylene lauryl ether acetic acid salt, and examples of the salt thereof include a sodium salt and a potassium salt.

Examples of the sulfosuccinic acid ester salt include a monoester or diester salt of sulfosuccinic acid with aliphatic alcohol (the number of carbon atoms is preferably 10 to 22, more preferably 12 to 18) or with polyoxyethylene alkyl ether (the number of carbon atoms in the alkyl group is preferably 10 to 22, more preferably 12 to 18, and the number of moles of ethylene oxide added is preferably 1 to 5), and examples of the salt include a sodium salt and a potassium salt. Specific examples include disodium lauryl sulfosuccinate, disodium lauryl polyoxyethylene sulfosuccinate, and sodium dialkyl sulfosuccinate.

The content of the component (A) in the first part is preferably 1 to 16% by mass, more preferably 2 to 14% by mass, and even more preferably 4 to 12% by mass.

[(B): Polymer or Copolymer Having a Mole Fraction of Diallyldimethyl Quaternary Ammonium Salt Monomer of not Less than 70%]

The two-part foam hair dye of the present invention at least comprises (B) a polymer or copolymer having a mole fraction of diallyldimethyl quaternary ammonium salt monomer of 70% or more in the first part. The polymer or copolymer of Component (B) improves fastness to shampooing by formation of complexes when a liquid mixture of the first part and the second part is diluted with water through interaction with Component (A). The polymer or copolymer of Component (B) needs to have the mole fraction of the diallyldimethyl quaternary ammonium salt monomer 70% or more. The mole fraction is more preferably 80% or more, and even more preferably 90% or more. In the case of a copolymer, no limitation is imposed on other monomers as long as they are copolymerizable; however, they preferably contain acrylic acid or acrylamide. Examples of such a polymer or copolymer include, as a commercially available product, Merquat 100 (mole fraction: 100%) and Merquat 295 (mole fraction: 95%) (the products of Nalco Company).

The content of the component (B) in the first part is preferably 0.2 to 5% by mass, more preferably 0.3 to 3% by mass, and even more preferably 0.5 to 2.5% by mass.

[Ratio of Component (A) to Component (B)]

The ratio of Component (A) to Component (B) in the first part is adjusted such that the equivalent ratio of the anion site of the component (A) to the cation site of the component (B) (anion/cation) is more than 1, taking into consideration that the content is stably present without separation when the first part and the second part are mixed, while it separates by formation of complexes when the mixture is diluted with water. Further, the ratio of Component (A) to Component (B) is preferably adjusted such that the equivalent ratio is 1.1 to 20, more preferably 1.2 to 10.

[(C): Oxidation Dye Having a Meta-Dihydroxybenzene Structure]

The first part of the two-part foam hair dye of the present invention comprises an oxidation dye having a meta-dihydroxybenzene structure as Component (C). Because the oxidation dye having a meta-dihydroxybenzene structure of the component (C) forms a complex with the polymer or copolymer of the component (B), containing a high concentration of such an oxidation dye causes the deterioration of the storage stability of the first part and the discharging properties of the liquid mixture. Nevertheless, regardless of the fact that the two-part foam hair dye of the present invention compresses a high concentration of the oxidation dye of the component (C), allowing polypropyleneglycol having a specific molecular weight as the component (D) to coexit inhibits the formation of a complex, allowing the two-part foam hair dye to exert good storage stability and good discharging properties from the foamer container. Examples of such an oxidation dye include resorcin, 2-methylresorcin, and 4-chlororesorcin.

The content of the oxidation dye of the component (C) in the first part is 0.5 to 1.5% by mass, preferably 0.52 to 1.45% by mass, and more preferably 0.55 to 1.4% by mass.

[(D): Polypropyleneglycol of a Weight-Average Molecular Weight of 200 to 1200]

The two-part foam hair dye of the present invention at least comprises (D) polypropyleneglycol of a weight-average molecular weight of 200 to 1200 in the first part. Inclusion of the component (D) not only markedly improves the storage stability at low temperature, but also improves the foam quality of the liquid mixture of the first part and the second part, and also achieves good hair dyeability. The weight-average molecular weight of polypropyleneglycol is preferably 250 to 1100, more preferably 300 to 800. Here, the weight-average molecular weight refers to a weight-average molecular weight in terms of polystyrene as measured by gel permeation chromatography (GPC).

From the viewpoint of excellent storage stability at low temperature, improved foam quality of the liquid mixture, and good applicability to the hair, the content of the component (D) in the first part is 0.1 to 9% by mass, preferably 0.3 to 8% by mass, and more preferably 0.5 to 6% by mass.

According to the present invention, from the viewpoint of excellent storage stability at low temperature and improved foam quality of the liquid mixture, a mass ratio of the content of the component (C) to the content of the component (D) ((C)/(D)) is no more than 5, preferably 0.05 to 4, and more preferably 0.06 to 3.

[Other Dyes]

The two-part foam hair dye of the present invention can comprise an oxidation dye other than the component (C) and a direct dye. Examples of the oxidation dye other than the component (C) include a dye precursor such as para-aminophenol, 4-amino-3-methylphenol, 6-amino-3-methylphenol, ortho-aminophenol, para-phenylenediamine, toluene-2,5-diamine, N,N-bis(2-hydroxyethyl)para-phenylenediamine, 2-(2-hydroxyethyl)para-phenylenediamine, and 1-hydroxyethyl-4,5-diaminopyrazole and a coupler such as meta-aminophenol, 5-amino-ortho-cresol, 5-(2-hydroxyethylamino)-2-methylphenol, 1-naphthol, meta-phenylenediamine, and 2,4-diaminophenoxyethanol. Also, examples of the direct dye include para-nitro-ortho-phenylenediamine, para-nitro-meta-phenylenediamine, Basic Yellow 87, Basic Orange 31, Basic Red 12, Basic Red 51, Basic Blue 99, and Acid Orange 7.

[Other Surfactants]

The two-part foam hair dye of the present invention can further comprise other surfactants in addition to the component (A) in either one or both of the first part and the second part so as to more easily form a foam by the foam discharge means of the foamer container and further stabilize the foam thus formed. In order to achieve good foaming allowing an easy application to the hair either when the liquid temperature is low or when it is close to normal temperature, the surfactant other than the component (A) is preferably an amphoteric surfactant or a nonionic surfactant.

Examples of the amphoteric surfactant include carbobetaine, amidobetaine, sulfobetaine, hydroxyl sulfobetaine, amidosulfobetaine, phospho-betaine, and imidazolinium surfactants having an alkyl group, an alkenyl group, or an acyl group with a carbon number of 8 to 24. Among them, a carbobetaine surfactant and a sulfobetaine surfactant are preferable. Preferred examples of the amphoteric surfactant include lauric acid amidopropyl betaine, coconut oil fatty acid amidopropyl betaine, lauryldimethylaminoacetic acid betaine, and laurylhydroxysulfobetaine. Two or more of the amphoteric surfactants can be used in combination. The content of the amphoteric surfactant in the liquid mixture of the first part and the second part is preferably 0.001 to 5% by mass, more preferably 0.002 to 2.5% by mass, and even more preferably 0.003 to 1% by mass.

Examples of the nonionic surfactant include an alkyl polyglucoside, a polyoxyalkylene alkyl ether, and an alkyl glyceryl ether. The carbon number of the alkyl group of the alkyl polyglucoside is preferably 8 to 18, more preferably 8 to 14, and even more preferably 9 to 11, and the alkyl group is preferably linear. The average degree of condensation of the glucoside is preferably 1 to 5, more preferably 1 to 2. The carbon number of the alkyl group of the polyoxyalkylene alkyl ether is preferably 10 to 22, more preferably 12 to 18, and the alkyl group is preferably linear. Also, the polyoxyethylene alkyl ether is more preferable, and especially the average addition mole number of the oxyethylene group of the polyoxyethylene alkyl ether is preferably 1 to 40, more preferably 4 to 30. The carbon number of the alkyl group of the alkyl glyceryl ether is preferably 8 to 18, more preferably 8 to 12, and the alkyl group is preferably branched. Two or more of the nonionic surfactants can be used in combination. The content of the nonionic surfactant in the liquid mixture of the first part and the second part is preferably 0.1 to 20% by mass, more preferably 0.2 to 15% by mass, and even more preferably 0.3 to 10% by mass.

[Higher Alcohol]

In order to improve the sustainability of foam and enhance the inhibitory effect on dripping while the hair dye is left on after the application to the hair, the two-part foam hair dye of the present invention can comprise a higher alcohol. As the higher alcohol, a higher alcohol having an alkyl group or an alkenyl group having 10 to 30 carbon atoms is preferable, a higher alcohol having an alkyl group or an alkenyl group having 12 to 24 carbon atoms is more preferable, and a higher alcohol having an alkyl group or an alkenyl group having 14 to 22 carbon atoms is even more preferable. Among them, a higher alcohol having an alkyl group is preferable, and a higher alcohol having a linear alkyl group is more preferable. Examples of the higher alcohol include myristyl alcohol, cetyl alcohol, stearyl alcohol, behenyl alcohol, isostearyl alcohol, and oleyl alcohol. Two or more of these higher alcohols can be used in combination.

Two or more of the higher alcohols can be used in combination, and the higher alcohol can be contained in either one or both of the first part and the second part. In order to enhance the inhibitory effect on dripping while the hair dye is left on without interfering with the foaming properties at a low liquid temperature, the content of the higher alcohol in the liquid mixture of the first part and the second part is 0.01 to 0.8% by mass, preferably 0.1 to 0.7% by mass, and more preferably 0.2 to 0.6% by mass.

[Non-Volatile Hydrophilic Solvent]

Further, the two-part foam hair dye of the present invention preferably comprises a non-volatile hydrophilic solvent in the first part or second part. Inclusion of a non-volatile hydrophilic solvent can alleviate irritation to the scalp caused by concentration of irritant components such as hydrogen peroxide due to evaporation of water from the two-part foam hair dye of the present invention, which occurs while the hair dye is left on after the application to the hair. As the non-volatile hydrophilic solvent, ones without the defoaming action such as polyols and lower (1 to 4 carbon atoms) alkyl ethers thereof are preferable. As the polyols, ones having 2 to 6 carbon atoms are preferable, and examples thereof include glycerin, propylene glycol, dipropylene glycol, 1,3-butanediol, ethylene glycol, diethylene glycol, isoprene glycol, and sorbitol. Examples of the lower alkyl ethers of polyol include mono lower alkyl ethers and poly lower alkyl ethers (such as a di-lower alkyl ether) of the polyols listed above. Among them, a monomethyl ether or a monoethyl ether of polyol is preferable, and specific examples include ethylene glycol monomethyl ether, ethylene glycol monoethyl ether, diethylene glycol monomethyl ether, and diethylene glycol monoethyl ether. Two or more of these ethers of polyols can be used in combination.

In consideration of the reducing effect on scalp irritation, and also for acquisition of good foam quality even at a low liquid temperature, the content of the non-volatile hydrophilic solvent in the liquid mixture of the first part and the second part is preferably 0.01 to 5% by mass, more preferably 0.1 to 4% by mass, and even more preferably 0.2 to 3% by mass.

[Silicones]

Silicones can be further added to the two-part foam hair dye of the present invention. Examples of the silicones include dimethylpolysiloxane, methylphenylpolysiloxane, polyether-modified silicone, amino-modified silicone, oxazoline-modified silicone elastomer, and emulsions of these silicones dispersed with a surfactant in water. Among them, polyether-modified silicone, amino-modified silicone, and emulsions of these silicones are preferable as they can stably disperse in water without using a thickener.

The polyether-modified silicone includes end-modified silicone and side chain-modified silicone, for example, pendant-type (comb-type) silicone, both end-modified silicone, and one end-modified silicone. Examples of the modified silicone include a dimethylsiloxane-methyl(polyoxyethylene)siloxane copolymer, a dimethylsiloxane-methyl(polyoxypropylene)siloxane copolymer, and a dimethylsiloxane-methyl(polyoxyethylene-polyoxypropylene)siloxane copolymer. The polyether-modified silicone has an HLB of preferably 10 or higher, more preferably 10 to 18, in view of compatibility with water. Here, HLB is a value obtained from a cloud number (cloud number: an index correlated with HLB, applicable to an ether type nonionic surfactant).

Amino-modified silicone having an amino group or an ammonium group may be used as the amino-modified silicone, and amodimethicone is preferred.

The content of silicones in the first part and the second part is preferably 0.01 to 10% by mass, more preferably 0.1 to 5% by mass, even more preferably 0.5 to 3% by mass for smooth blending of foam into the hair, and for impartation of high conditioning effects to the hair.

[Other Components]

Besides the components mentioned above, the first part and the second part can contain fragrance, an ultraviolet ray absorber, a sequestering agent such as edetic acid, a disinfectant, a preservative such as methyl parahydroxybenzoate, phenacetin, 1-hydroxyethane-1,1-diphosphonic acid, a stabilizer such as oxyquinoline sulfate, an organic solvent such as ethanol, benzyl alcohol, and benzyloxy ethanol, a water-soluble polymer compound such as hydroxyethylcellulose, a humectant, and the like in accordance with the intended use. Also, the liquid mixture of the first part and the second part is preferably a medium mainly composed of water.

The oxidative hair dye composition of the present invention is provided as a two-part oxidative hair dye which contains the first part containing an alkali agent and the second part containing hydrogen peroxide. Here, the "two-part" also encompasses a three-part type oxidative hair dye, which is used by further mixing, in addition to the aforementioned first part and second part, a third part containing, for example, persulfate or a conditioning agent. The mixing ratio of the first part to the second part is preferably 1:4 to 4:1, more preferably 1:2 to 2:1 in terms of mass ratio.

[Viscosity]

The viscosity of the liquid mixture of the first part and the second part is 1 to 300 mPa·s, preferably 2 to 200 mPa·s, more preferably 3 to 100 mPa·s, and even more preferably 5 to 30 mPa·s. It is to be noted that the viscosity as referred to herein refers to a value obtained after rotating the liquid mixture at 60 rpm for one minute at 25° C. by a B-type rotational viscometer (model TV-10), manufactured by TOKYO KEIKI INC., with rotor No. 1 or 2. When the object to be measured has a viscosity of less than 100 mPa·s, the viscosity is measured using rotor No. 1, whereas when it has a viscosity of 100 to 499 mPa·s, the viscosity is measured using rotor No. 2. It should be noted that the measurement is made in a thermostat bath at 25° C. immediately after mixing the first part and the second part, and temperature fluctuations caused by heat of reaction are negligible.

As the viscosity of a liquid mixture of the first part and the second part is adjusted to be in the aforementioned range, easily-applicable foam volume can be realized and dripping of the liquid mixture applied to the hair can be prevented, while squeezing to discharge a foam from, for example, a squeeze foamer becomes easy. In order to adjust the viscosity of the liquid mixture to the aforementioned range, a water-soluble solvent such as ethanol may be added, or the content and the kind of, for example, a surfactant, a polyol, a higher alcohol, may be appropriately adjusted.

[Gas-Liquid Mixing Ratio]

The gas-liquid mixing ratio of air and the liquid mixture achieved by the foam discharge means of the foamer container is preferably 7 to 40 mL/g, more preferably 15 to 30 mL/g, in view of easy blending of the preparation into the hair and easy application. The gas-liquid mixing ratio referred to herein is a value measured as follows.

Firstly, the mass and the volume of a foam discharged at 25° C. are measured to obtain a gas-liquid mixing ratio. Into a S1 squeeze foamer (Daiwa Can Company, a volume of 210 mL, the mesh coarseness (aperture) in a mixing chamber is 150 mesh (150 openings per inch (25.4 mm)), and that of a mesh closest to the discharge outlet is 200 mesh), 100 g of the liquid mixture is placed. Once the amount of remaining foam has reached 80 g, 20 g of foam is discharged into a 1000 mL graduated cylinder, and the volume of foam thus discharged is measured one minute after initiation of discharging. The volume of discharged foam thus obtained (mL) is divided by a mass of 20 g to give a gas-liquid mixing ratio (mL/g).

[Foamer Container]

In the present invention, a foamer container is a non-aerosol type container, which is used to discharge a liquid mixture of the first part and the second part in the form of a foam by mixing it with air without using a propellant. Spattering of discharged preparation can also be prevented with use of a foamer container. Among foamer containers, a non-aerosol type container can be produced at a lower cost than an aerosol type container, and it can be handled more safely during distribution as no high-pressure gas propellant needs to be used.

As the non-aerosol foamer container, for example, a publicly-known pump foamer container with foam discharge means, a squeeze foamer container, an electric foamer, and an accumulator pump foamer container can be used. Specific examples thereof include pump foamer E3 type, pump foamer F2 type [the products of Daiwa Can Company, "Food & Packaging" (vol. 35, No. 10, pages 588 to 593 (1994); vol. 35, No. 11, pages 624 to 627 (1994); vol. 36, No. 3, pages 154 to 158 (1995))], a S1 squeeze foamer (Daiwa Can Company, JP-A-7-215352), an electric foamer (Matsushita Electric Works, Ltd.), and an air spray foamer (Airspray International, Inc.). As the foamer container to be used for the two-part foam hair dye of the present invention, a pump foamer container and a squeeze foamer container are preferable as they are inexpensive and can be handled easily.

A pump foamer container or a squeeze foamer container has a foam-forming means such as a net. It preferably has a thin net so that, in a case that a liquid mixture of the first part and the second part is dried and solidified to cause clogging, the flow of foam generated by the next discharging immediately dissolves the solidified mass to resolve the clogging. In this case, the mesh of the net is preferably 50 to 280 mesh, more preferably 90 to 250 mesh, and even more preferably 130 to 220 mesh. Here, a mesh refers to the number of apertures per inch. Use of the net of the mesh within the above range enables formation of a creamy foam. Also, preferred examples of the material of the mesh include, for example, nylon, polyethylene, polypropylene, polyester, Teflon (Registered Trademark), carbon fiber, stainless, more preferably nylon, polyethylene, polypropylene and polyester, and more preferably nylon.

In the non-aerosol foamer container used in the two-part foam hair dye of the present invention, preferably at least one sheet, more preferably more than one sheets of such a net are set. In view of economic efficiency, foam stability, and the like, it is preferable to set one sheet in a mixing chamber and one sheet at the tip of the discharge outlet.

The part of the non-aerosol foamer container which is in contact with the content (for example, the inner wall of the container, the inner wall of the foam discharge means) is preferably composed of a material resistant to corrosion by alkali and hydrogen peroxide while allowing permeation of oxygen generated by decomposition of hydrogen peroxide.

As the product form of the two-part foam hair dye of the present invention composed of the first part, the second part, and the non-aerosol foamer container, the first part and the second part may each be contained in containers separate from the non-aerosol foamer container, and they may be transferred to the non-aerosol foamer container and mixed upon application. Alternatively, one of the parts is contained in the non-aerosol foamer container while the other is contained in a separate container, and the part in the separate container may be transferred to the non-aerosol foamer container upon application. In this case, the second part is contained in a gas-permeable container, especially a non-aerosol foamer container composed of an oxygen-permeable material (for example, polyethylene) for prevention of an increase in the pressure inside the container due to oxygen generated by decomposition of hydrogen peroxide. Meanwhile, a container through which oxygen hardly permeates needs to be used for the first part for prevention of oxidation of the oxidation dye.

[Application Method]

In order to dye the hair (particularly, the hair of the head) with the two-part foam hair dye of the present invention, the hair is preferably combed in advance. Because the hair becomes less likely to get tangled by combing during the re-foaming treatment to be described below, there is no fear of splattering of the liquid mixture. Further, after combing the hair, blocking needs not be performed, which is usually performed in application of a hair dye composition. Furthermore, blocking is preferably not performed. Absence of blocking makes the below-described operation of application of a hair dye composition to the hair and re-foaming operation easy. Subsequently, the first part and the second part of the two-part hair dye of the present invention are mixed in the non-aerosol foamer container. The liquid mixture discharged in the form of a foam from the container may be applied to the hair directly or using a tool such as hands or a brush. From the viewpoint of prevention of splattering and dripping of the part, the part is preferably discharged in (gloved) hands first, and then applied to the hair.

After application, the hair dye product is left on the hair for approximately 3 to 60 minutes, preferably approximately 5 to 45 minutes. At this time, from the viewpoint of ensuring prevention of dripping while the hair dye product is left on the hair and adequately covering also the hair root with the liquid mixture, the hair dye product is preferably re-foamed on the hair. For re-foaming, gas may be infused, a tool such as a vibrating device and a brush or fingers may be used, and fingers are more preferably used.

At this point, re-foaming may be performed after complete disappearance of the foam, during disappearance of the foam, or before the foam applied undergoes changes. Alternatively, re-foaming may be performed after completion of application of the foam to the entire range of areas to which the hair dye product is intended to be applied or during application. Re-foaming may be performed continuously once or intermittently repeated multiple times.

After these operations, the liquid mixture is rinsed off. Subsequently, the hair is appropriately shampooed and conditioned, and then rinsed with water, followed by drying.

EXAMPLES

Examples 1 to 9, Comparative Examples 1 to 7

The first parts having the compositions as shown in Table 1 (% by mass) and the second parts shown below were prepared, and "low-temperature stability of the first part", "foam quality of the liquid mixture", and "fastness to shampooing" were evaluated.

|  | (% by mass) |
|---|---|
| Stearyl trimethyl ammonium chloride | 0.84 |
| Polyoxyethylene (40) cetyl ether | 0.55 |
| Cetanol | 0.88 |
| Myristyl alcohol | 0.25 |
| Hydroxyethane diphosphonic acid | 0.04 |
| Oxyquinoline sulfate (2) | 0.04 |
| Sodium hydroxide or phosphoric acid | In an amount that adjusts pH of the second part to 3.6 |
| Hydrogen peroxide | 5.7 |
| Purified water | Balance |

[Low-Temperature Stability of the First Part]

The first parts having the compositions as shown in Table 1 were sealed in containers and left in a constant temperature room at 5° C. for one month. Subsequently, visual evaluation was made based on the following criteria.
- a: no change was observed
- b: slight turbidity was observed
- c: white turbidity was observed

[Foam Quality of the Liquid Mixture]

The first parts having the compositions as shown in Table 1 and the aforementioned second parts were mixed at a mass ratio of 1:1.5 in a squeeze foamer (S1 squeeze foamer manufactured by Daiwa Can Company, a volume of 210 mL, the mesh coarseness in a mixing chamber is 150 mesh and that of a mesh closest to the discharge outlet is 200 mesh, the total area of the narrowest opening of an air induction passage is 0.27 mm², and the inner diameter of a dip tube is 1.7 mm). The liquid mixture was then discharged in the form of a foam and observed for its foam quality.
- a: excellent shape retention property with fine foam
- b: good shape retention property with fine foam
- c: slightly loose foam or slightly coarse foam
- d: loose foam or coarse foam
- e: watery foam or coarse foam with numerous large foams

[Fastness to Shampooing]

The first part and the second part were prepared, which were mixed at a mass ratio of 1:1.5 to prepare a liquid mixture. Four tresses of Chinese white hair manufactured by Beaulax Co., Ltd., each weighing 1 g and being 10 cm in length, were prepared for each Example and Comparative Example.

The liquid mixture of 30° C. was discharged in the form of a foam from a squeeze foamer (S1 squeeze foamer manufactured by Daiwa Can Company, a volume of 210 mL, the mesh coarseness in a mixing chamber is 150 mesh and that of a mesh closest to the discharge outlet is 200 mesh, the total area of the narrowest opening of an air induction passage is 0.27 mm², and the inner diameter of a dip tube is 1.7 mm). The foam of the liquid mixture was applied to the hair in a ratio of 1 to 1, and then left for 30 minutes. Subsequently, the four tresses were immersed in 100 mL of ion exchange water all together, and left for one minute. Then, the tresses were shampooed using a shampoo shown below and dried, which served as evaluation samples of pre-shampooed hair.

The value of color difference $\Delta E_0$ from before hair dyeing was measured in the evaluation samples thus obtained by using a colorimeter CR-400 manufactured by Konica Minolta Sensing, Inc. Two tresses with median $\Delta E_0$ values were used in the following tests. The evaluation samples were each tress placed in a test tube NS-10 manufactured by As One Corporation. The tubes were adequately filled with a 10-fold diluted solution of the shampoo shown below and sealed. Subsequently, the samples were treated at 40° C. and a shaking speed of 120 rpm using a water bath shaker MM-10 manufactured by TAITEC Corporation for 30 minutes. After treatment, the tresses were rinsed with water and dried, which served as evaluation samples of shampooed hair. The value of color difference $\Delta E_1$ from before hair dyeing was measured also in the evaluation samples of shampooed hair by using the aforementioned colorimeter. Fastness to shampooing was evaluated according to the following evaluation criteria.

Comparing the difference between $\Delta E_0$ before shampooing and $\Delta E_1$ after shampooing ($\Delta E_0 - \Delta E_1$) with that of Comparative Example 3 (standard; ($\Delta E_0 - \Delta E_1 = 2.3$), the following evaluation was made:
- a: smaller by 1 or greater
- b: smaller by 0.5 or greater to less than 1
- c: equivalent (within ±0.5)
- d: larger by 0.5 or greater

| (Shampoo used for evaluation) | |
|---|---|
| Sodium POE (3) lauryl ether sulfate | 15.5% by mass |
| Lauric acid diethanolamide | 1.5% by mass |
| Tetrasodium edetate | 0.3% by mass |
| Sodium benzoate | 1.43% by mass |
| Deionized water | Balance |

TABLE 1

| First part (% by mass; the content entirely represents the active amount) | Example | | | | | | | | |
|---|---|---|---|---|---|---|---|---|---|
|  | 1 | 2 | 3 | 4 | 5 | 6 | 7 | 8 | 9 |
| toluene-2,5-diamine | 1.11 | 1.11 | 1.11 | 1.11 | 1.55 | 0.55 | 0.98 | 1.11 | 1.11 |
| (C) resorcin | 1.00 | 1.00 | 1.00 | 1.00 | 1.40 | 0.50 | — | 1.00 | 1.00 |
| (C) 2-methylresorcin | — | — | — | — | — | — | 1.00 | — | — |
| (A) sodium polyoxyethylene (5) lauryl ether acetate | 2.00 | 2.00 | 2.00 | 2.00 | 2.00 | 2.00 | 2.00 | 2.00 | 2.00 |
| (A) sodium cocoyl glutamate | 6.00 | 6.00 | 6.00 | 6.00 | 6.00 | 6.00 | 6.00 | 6.00 | 6.00 |
| (A)' sodium polyoxyethylene lauryl ether sulfate (2.0 E.O.) | — | — | — | — | — | — | — | — | — |
| alkyl (8 to 16) glucoside | 2.00 | 2.00 | 2.00 | 2.00 | 2.00 | 2.00 | 2.00 | 2.00 | 2.00 |
| polyoxyethylene lauryl ether (23 E.O.) | 2.00 | 2.00 | 2.00 | 2.00 | 2.00 | 2.00 | 2.00 | 2.00 | 2.00 |
| polyoxyethylene tridecyl ether | 0.50 | 0.50 | 0.50 | 0.50 | 0.50 | 0.50 | 0.50 | 0.50 | 0.50 |

TABLE 1-continued

| First part (% by mass; the content entirely represents the active amount) | | | | | | | | | |
|---|---|---|---|---|---|---|---|---|---|
| (D) polypropylene glycol (weight-average molecular weight 400) | 6.00 | 0.30 | 4.00 | 9.00 | 6.00 | 6.00 | 6.00 | — | — |
| (D) polypropylene glycol (weight-average molecular weight 700) | — | — | — | — | — | — | — | 4.00 | — |
| (D) polypropylene glycol (weight-average molecular weight 1000) | — | — | — | — | — | — | — | — | 4.00 |
| (D)' polypropylene glycol (weight-average molecular weight 2000) | — | — | — | — | — | — | — | — | — |
| (B) dimethyldiallylammonium chloride-acrylic acid copolymer (*1) | 1.20 | 1.20 | 1.20 | 1.20 | 1.20 | 1.20 | 1.20 | 1.20 | 1.20 |
| ammonia | 1.12 | 1.12 | 1.12 | 1.12 | 1.12 | 1.12 | 1.12 | 1.12 | 1.12 |
| ammonium bicarbonate | 3.40 | 3.40 | 3.40 | 3.40 | 3.40 | 3.40 | 3.40 | 3.40 | 3.40 |
| monoethanolamine | 0.80 | 0.80 | 0.80 | 0.80 | 0.80 | 0.80 | 0.80 | 0.80 | 0.80 |
| ethanol | 9.50 | 9.50 | 9.50 | 9.50 | 9.50 | 9.50 | 9.50 | 9.50 | 9.50 |
| ascorbic acid | q.s. | q.s. | q.s. | q.s. | q.s. | q.s. | q.s. | q.s. | q.s. |
| anhydrous sodium bisulfite | q.s. | q.s. | q.s. | q.s. | q.s. | q.s. | q.s. | q.s. | q.s. |
| tetrasodium edetate dihydrate | q.s. | q.s. | q.s. | q.s. | q.s. | q.s. | q.s. | q.s. | q.s. |
| purified water | balance | balance | balance | balance | balance | balance | balance | balance | balance |
| anion/cation equivalent ratio of Component (A)/Component (B) | 2.6 | 2.6 | 2.6 | 2.6 | 2.6 | 2.6 | 2.6 | 2.6 | 2.6 |
| mass ratio of Component (C)/Component (D) | 0.17 | 3.33 | 0.25 | 0.11 | 0.23 | 0.08 | 0.17 | 0.25 | 0.25 |
| viscosity of the liquid mixture (25° C., mPa·s) | 12 | 12 | 11 | 12 | 11 | 12 | 11 | 11 | 10 |
| evaluation  low-temperature stability (5° C.) | a | a | a | a | a | a | a | a | a |
| foaming properties at room temperature (25° C.) | a | b | a | a | a | a | a | a | a |
| fastness | a (0.75) | a (0.07) | a (0.71) | a (0.10) | a (0.46) | b (1.67) | a (0.10) | a (0.40) | a (0.43) |

| First part (% by mass; the content entirely represents the active amount) | Comparative Example | | | | | | |
|---|---|---|---|---|---|---|---|
| | 1 | 2 | 3 | 4 | 5 | 6 | 7 |
| toluene-2,5-diamine | 1.11 | 1.11 | 1.11 | 1.11 | 1.11 | 2.00 | 1.11 |
| (C) resorcin | 1.00 | 1.00 | 1.00 | 1.00 | 1.00 | 1.80 | 1.00 |
| (C) 2-methylresorcin | — | — | — | — | — | — | — |
| (A) sodium polyoxyethylene (5) lauryl ether acetate | 2.00 | 2.00 | 2.00 | — | 2.00 | 2.00 | 2.00 |
| (A) sodium cocoyl glutamate | 6.00 | 6.00 | 6.00 | — | 6.00 | 6.00 | 6.00 |
| (A)' sodium polyoxyethylene lauryl ether sulfate (2.0 E.O.) | — | — | — | 7.20 | — | — | — |
| alkyl (8 to 16) glucoside | 2.00 | 2.00 | 2.00 | 2.00 | 2.00 | 2.00 | 2.00 |
| polyoxyethylene lauryl ether (23 E.O.) | 2.00 | 2.00 | 2.00 | 2.00 | 2.00 | 2.00 | 2.00 |
| polyoxyethylene tridecyl ether | 0.50 | 0.50 | 0.50 | 0.50 | 0.50 | 0.50 | 0.50 |
| (D) polypropylene glycol (weight-average molecular weight 400) | — | 10.00 | 6.00 | 6.00 | 0.10 | 6.00 | — |
| (D) polypropylene glycol (weight-average molecular weight 700) | — | — | — | — | — | — | — |
| (D) polypropylene glycol (weight-average molecular weight 1000) | — | — | — | — | — | — | — |
| (D)' polypropylene glycol (weight-average molecular weight 2000) | — | — | — | — | — | — | 4.00 |
| (B) dimethyldiallylammonium chloride-acrylic acid copolymer (*1) | 1.20 | 1.20 | — | 1.20 | 1.20 | 1.20 | 1.20 |
| ammonia | 1.12 | 1.12 | 1.12 | 1.12 | 1.12 | 1.12 | 1.12 |
| ammonium bicarbonate | 3.40 | 3.40 | 3.40 | 3.40 | 3.40 | 3.40 | 3.40 |
| monoethanolamine | 0.80 | 0.80 | 0.80 | 0.80 | 0.80 | 0.80 | 0.80 |
| ethanol | 9.50 | 9.50 | 9.50 | 9.50 | 9.50 | 9.50 | 9.50 |
| ascorbic acid | q.s. | q.s. | q.s. | q.s. | q.s. | q.s. | q.s. |
| anhydrous sodium bisulfite | q.s. | q.s. | q.s. | q.s. | q.s. | q.s. | q.s. |
| tetrasodium edetate dihydrate | q.s. | q.s. | q.s. | q.s. | q.s. | q.s. | q.s. |
| purified water | balance | balance | balance | balance | balance | balance | balance |
| anion/cation equivalent ratio of Component (A)/Component (B) | 2.6 | 2.6 | — | 2.6 | 2.6 | 2.6 | 2.6 |
| mass ratio of Component (C)/Component (D) | — | 0.10 | 0.17 | 0.17 | 10 | 0.33 | 0.25 |
| viscosity of the liquid mixture (25° C., mPa·s) | 12 | 10 | 10 | — | 11 | 10 | — |
| evaluation  low-temperature stability (5° C.) | b | a | a | a | b | c | *2 |
| foaming properties at room temperature (25° C.) | d | c | b | *2 | c | a | *2 |
| fastness | a (0.85) | a (0.93) | standard (2.3) | *2 | b (1.67) | a (0.43) | *2 |

*1 Merquat 295, the product of Nalco Company; the mole fraction of cationic monomers was 95%.
*2 Unmeasurable due to separation

The invention claimed is:

1. A two-part foam hair dye which comprises a first part comprising an alkali agent, a second part comprising hydrogen peroxide, and a non-aerosol foamer container for discharging a liquid mixture of the first part and the second part in the form of a foam,
wherein the first part comprises components (A) to (D), the equivalent ratio of the anion site of the component (A) to the cation site of the component (B) (anion/cation) is more than 1, a mass ratio of the content of the component (C) to the content of the component (D), (C)/(D), is 5 or less, and a viscosity of the liquid mixture at 25° C. is 1 to 300 mPa·s:
(A) a carboxylic acid anionic surfactant,
(B) a polymer or copolymer having a mole fraction of diallyldimethyl quaternary ammonium salt monomer of 70% or more,
(C) 0.5 to 1.5% by mass of an oxidation dye having a meta-dihydroxybenzene structure, and
(D) 0.1 to 9% by mass of polypropyleneglycol of a weight-average molecular weight of 200 to 1200.

2. The two-part foam hair dye according to claim 1, wherein the component (C) is an oxidation dye selected from the group consisting of resorcin, 2-methylresorcin, and 4-chlororesorcin.

3. The two-part foam hair dye according to claim 1, wherein the component (A) is one or more members selected from the group consisting of an N-acylamino acid salt, an N-acyl-N-alkylamino acid salt, an ether carboxylic acid salt, and a sulfosuccinic acid ester salt.

4. The two-part foam hair dye according to claim 1, wherein a content of the component (A) in the first part is 1 to 16% by mass.

5. The two-part foam hair dye according to claim 1, wherein a content of the component (B) in the first part is 0.2 to 5% by mass.

6. The two-part foam hair dye according to claim 3, wherein an amino acid residue of the N-acylamino acid salt of the component (A) is one or more members selected from the group consisting of glutamic acid and aspartic acid.

7. The two-part foam hair dye according to claim 3, wherein the N-acylamino acid salt of the component (A) is one or more members selected from the group consisting of N-lauroyl glutamate, N-myristoyl glutamate, N-stearoyl glutamate, N-cocoyl glutamate, and N-hydrogenated tallow glutamate.

8. The two-part foam hair dye according to claim 3, wherein an amino acid residue of the N-acyl-N-alkylamino acid salt of the component (A) is one or more members selected from the group consisting of glutamic acid, glycine, and β-alanine.

9. The two-part foam hair dye according to claim 3, wherein the N-acyl-N-alkylamino acid salt of the component (A) is one or more members selected from the group consisting of an N-lauroyl-N-isopropyl glycine salt, an N-lauroyl sarcosine salt, an N-myristoyl sarcosine salt, an N-palmitoyl sarcosine salt, and an N-lauroyl-N-methyl-β-alanine salt.

10. The two-part foam hair dye according to claim 3, wherein the ether carboxylic acid salt of the component (A) is one or more members selected from the group consisting of a polyglyceryl alkyl ether acetic acid salt and an ether acetic acid salt represented by general formula (I):

$$R\text{—}Z\text{—}(CH_2CH_2O)_m\text{—}CH_2CO_2X \qquad (1)$$

wherein, R represents a linear or branched alkyl group or alkenyl group having 7 to 19 carbon atoms, Z represents —O— or —CONH—, X represents a hydrogen atom, an alkali metal, triethanolamine, or ammonium, and m represents a number of 1 to 20.

11. The two-part foam hair dye according to claim 10, wherein the ether acetic acid salt is one or more members selected from the group consisting of a polyoxyethylene (10) lauryl ether acetic acid salt, a polyoxyethylene (8) myristyl ether acetic acid salt, a lauric acid amide polyoxyethylene (6) ether acetic acid salt, a lauric acid amide polyoxyethylene (10) ether acetic acid salt, a polyoxyethylene tridecyl ether acetic acid salt, and a polyoxyethylene lauryl ether acetic acid salt.

12. The two-part foam hair dye according to claim 3, wherein the sulfosuccinic acid ester salt of the component (A) is a monoester or diester salt formed from sulfosuccinic acid and aliphatic alcohol (a number of carbon atoms is 10 to 22) or polyoxyethylene alkyl ether (a number of carbon atoms in the alkyl group is 10 to 22 and a number of moles of ethylene oxide added is 1 to 5).

13. The two-part foam hair dye according to claim 3, wherein the sulfosuccinic acid ester salt of the component (A) is one or more members selected from the group consisting of disodium lauryl sulfosuccinate, disodium lauryl polyoxyethylene sulfosuccinate, and sodium dialkyl sulfosuccinate.

14. A method for dyeing hair with the two-part foam hair dye according to claim 1, the method comprising mixing the first part and the second part in the non-aerosol foamer container, and subsequently, discharging a liquid mixture in the form of a foam from the container on a hand, and then applying the liquid mixture to hair, and after leaving the liquid mixture on for 3 to 60 minutes, rinsing the liquid mixture off.

15. The method for dyeing hair according to claim 14, further comprising, after applying the liquid mixture in the form of a foam to hair, re-foaming the liquid mixture on the hair with fingers before rinsing the liquid mixture off.

* * * * *